United States Patent
Croft et al.

(10) Patent No.: US 7,033,333 B1
(45) Date of Patent: Apr. 25, 2006

(54) SELF ACTUATED CERVICAL (NECK) TRACTION DEVICE

(76) Inventors: Arthur Croft, 2731 Via Orange Way, Ste. 105, Spring Valley, CA (US) 91978; Michael Haneline, 1112 Avacado Summit Dr., El Cajon, CA (US) 92019

(*) Notice: Subject to any disclaimer, the term of this patent is extended or adjusted under 35 U.S.C. 154(b) by 0 days.

(21) Appl. No.: 10/628,266

(22) Filed: Jul. 29, 2003

Related U.S. Application Data (60) Provisional application No. 60/400,125, filed on Aug. 2, 2002.

(51) Int. Cl.
*A61F 5/00* (2006.01)

(52) U.S. Cl. .............. 602/36; 602/17; 602/18

(58) Field of Classification Search ......... 602/32–39, 602/241, 17–19, 78; 128/75, 846, 97.1, 845, 128/207.17, DIG. 23, DIG. 15; 482/10; D24/191; 601/39; 2/425
See application file for complete search history.

(56) References Cited

U.S. PATENT DOCUMENTS

| | | | | |
|---|---|---|---|---|
| 923,862 A * | 6/1909 | Langworthy | ........ | 602/36 |
| 1,837,153 A * | 12/1931 | Ettinger | ........ | 602/36 |
| 2,151,458 A * | 3/1939 | Allen | ........ | 602/17 |
| 2,183,265 A * | 12/1939 | Maloney | ........ | 482/95 |
| 2,740,399 A * | 4/1956 | Judovich | ........ | 602/36 |
| 2,954,026 A | 9/1960 | Spinks | | |
| 3,114,366 A | 12/1963 | Haychark | | |
| 3,540,439 A * | 11/1970 | Gaylord, Jr. | ........ | 602/36 |
| 3,871,366 A | 3/1975 | Cotrell | | |
| 4,010,744 A | 3/1977 | Boyen | | |
| 4,236,265 A * | 12/1980 | Carradine | ........ | 5/630 |
| 4,383,524 A | 5/1983 | Boger | | |
| 4,407,274 A * | 10/1983 | Goodley | ........ | 606/241 |
| 4,580,554 A | 4/1986 | Goodley | | |
| 4,685,671 A * | 8/1987 | Hagerman et al. | ........ | 482/124 |
| 4,971,043 A | 11/1990 | Jones | | |
| 5,024,214 A | 6/1991 | Hayes | | |
| 5,052,378 A * | 10/1991 | Chitwood | ........ | 606/242 |
| 5,078,126 A * | 1/1992 | Perry | | |
| 5,129,881 A * | 7/1992 | Pope | ........ | 602/32 |
| 5,131,410 A * | 7/1992 | Neill et al. | ........ | 5/657 |
| 5,176,707 A | 1/1993 | Phillips | | |
| 5,258,017 A | 11/1993 | Myers et al. | | |
| 5,267,352 A * | 12/1993 | Rodarmel | ........ | 2/44 |

(Continued)

FOREIGN PATENT DOCUMENTS

GB          2203348 A  * 10/1988

*Primary Examiner*—Henry Bennett
*Assistant Examiner*—Shumaya B. Ali
(74) *Attorney, Agent, or Firm*—Tom Hamill, Jr.

(57) ABSTRACT

A self-actuated cervical traction device is provided. The traction device includes a headpiece, a loop attached to the headpiece, a cord, a pulley and a foot engaging loop. The headpiece is secured on the head. The headpiece includes straps which are connected to a first anchor. The cord is first connected to the first anchor and then to and through the pulley system. The pulley system is supported by a door. The cord is further connected to a second anchor. The second anchor is further connected to a foot strap, which engages the feet of the user. The headpiece would be adjusted, and the user would lie on the floor. When the user extends their legs, the foot loop transmits force back through to the headpiece through the cord and pully system stretching the muscles at the back of the neck, causing a therapeutic effect.

7 Claims, 8 Drawing Sheets

U.S. PATENT DOCUMENTS

| | | |
|---|---|---|
| 5,451,202 A | 9/1995 | Miller et al. |
| 5,685,021 A * | 11/1997 | Tsujino ............................ 2/425 |
| 5,713,841 A * | 2/1998 | Graham ........................ 602/32 |
| 5,867,834 A * | 2/1999 | Simpson ......................... 2/174 |
| 5,964,506 A * | 10/1999 | Coates et al. ................ 297/484 |
| 6,113,563 A | 9/2000 | D'Amico et al. |
| 6,200,285 B1 * | 3/2001 | Towliat ....................... 602/18 |
| 6,418,565 B1 * | 7/2002 | Tsujino ............................ 2/425 |
| 6,511,450 B1 * | 1/2003 | Bauermeister ............... 602/33 |
| 6,607,245 B1 * | 8/2003 | Scher .......................... 297/393 |
| 6,613,563 B1 * | 9/2003 | Sosnowski et al. ....... 435/320.1 |
| 6,648,416 B1 * | 11/2003 | O'Connor et al. .......... 297/397 |
| 6,668,834 B1 * | 12/2003 | Zikria ......................... 128/848 |
| 2004/0144390 A1 * | 7/2004 | Taylor-Kennedy .......... 128/846 |

* cited by examiner

SELF ACTUATED CERVICAL (NECK) TRACTION DEVICE

RELATED APPLICATIONS

This application claims the benefit of U.S. Provisional Patent Application 60/400,125 filed on Aug. 2, 2002 and is herein incorporated by reference.

BACKGROUND OF THE INVENTION

1. Field of the Invention

The present invention relates to the traction devices. More particularly, this invention relates to a cervical traction device which may be employed by a patient in an out-patient or in-patient setting. The instant invention is known as the EasyTrak, TM. It was developed at the Spine Research Institute of San Diego.

2. Description of the Invention

Cervical traction stretches the muscles, ligaments, and discs of the neck. It provides relief by separating the spaces between the neck bones, which contain the nerves and disks, and may reduce pressure on the structures within the nerve openings. Cervical traction is not indicated for use in some conditions of instability such as fractures, dislocations, and some advanced disc problems.

Cervical traction is most helpful when used lying on the back with the neck placed in flexion (tilting forward). Using traction in this position helps stretch the muscles at the back of the neck and allow separation of the bones in the neck. This relieves pressure that may be pinching nerves and consequently, promotes muscle relaxation. Health care professionals often provide home traction programs for chronic cervical pain patients to encourage self management.

In order to provide a simple and easy to use home traction device the following self-actuated cervical (neck) traction device is provided.

The traction device includes a headpiece. This headpiece is unique and includes structure for supporting the neck in the most desirable position for cervical traction. A description of the structure follows.

The headpiece includes a rear element, the rear element being generally rectangular. The rear element is manufactured from a comfortable fabric, including, but not limited to, neoprene rubber.

The rear element has a front side which is designed to be placed against the neck and a back side which does not come in contact with the neck.

The back side of the rear element includes a nylon webbing which is affixed thereto. The webbing may be affixed in any conventional way, including, but not limited to, stitching, ultrasonic welding, or adhesives. The nylon webbing is affixed to a major portion of the rear element. This webbing gives the rear element extra support and is to be positioned on a specific region of the patient's neck.

On the right and left side the webbing is no longer affixed to the back side of the rear element and circles about to a first anchor located in the front of the headpiece. The webbing is affixed in what may be termed an open trapezoidal configuration, or an extended U-shape, and will be shown in the accompanying sketches and diagrams.

The back side of the rear element includes a right side and a left side. To the right side of the rear element is a first (right) connection element affixed to the back side of the rear element after the webbing mentioned above is no longer attached. To the left side of the rear element is a second (left) connection element affixed to the rear element after the webbing mentioned above is no longer attached.

The first connection element and the second connection element are securely affixed and have a generally vertical rectangular aperture located thereon. There is a first vertical rectangular aperture located on the right side, and a second vertical rectangular aperture located on the left side.

A first strap is provided. The first strap has a first side, a second side, a right side, a middle side and a left side. On the first strap first side is a cushioned portion, the cushioned portion being located on the middle side.

On the first strap second side the following configuration is found. On the left side is a plurality hooks associated with hook and loop fasteners. This is followed by a first portion of the strap. This is followed by a plurality of loops associated with hook and loop fasteners. The loops are located on the middle side. This is followed by a second portion of the strap. This is then followed by the right side which includes a plurality of hooks associated with hook and loop fasteners.

The rear element front side is placed against the patients neck, with the affixed webbed portion to be placed proximal the lowest part of the back of the skull. In this configuration, the neoprene rubber will be intermediate the webbing and the neck.

Then the first strap first side is placed on the forehead of the patient with the cushioned portion residing directly on the forehead. The first strap right side is placed through the first vertical rectangular aperture on the right side. The first strap left side is place through the second vertical rectangular aperture on the left side. On both the right and left side the strap should be pulled through its associated aperture until it reaches the portion of the strap which has no hook and loop fasteners located thereon. At that point, the strap is adjusted for comfort, and is bent about both the right and left apertures. This affixes the hook fasteners on both the right and left ends of the strap with the loop fasteners located on the middle of the strap, firmly securing the headpiece about the patients head. During the application of the headpiece, the patient should remove their eyeglasses. Also, hair should be positioned outside the headpiece.

At this point, the webbing with the anchor is pulled forward, basically parallel to the strap surrounding the head of the patient. The first anchor at the end of the webbing is attached to a cord. This attachment may be by a knot or another means of attachment.

A pulley system is placed in a door, with the door securing the pulley in place. This is done by placing a ball on the end of a cord which is then connected to the pulley. When the door closes on the cord intermediate the ball and the pulley, the pulley is secured in place on one side of the door and the ball is secured in place on the other side of the door. The pulley acts as a force redirection means. Other devices may be used to redirect the force of the cord other than a pulley. Further, it is to be understood that other systems have been contemplated for mounting the pulley at an appropriate location and this system is not designed to be limiting. The ball (sphere) may be a square, rectangle, octagon or any other geometrical shape. This may be placed in a door with hinges and a knob, a sliding glass door, or other structure which has an open and closed position. For the sake of safety, one should ensure that the door not be opened while the therapy is proceeding. This may be done by a sign or other indicating means. In addition, the cord may be made from any material which has sufficient material properties to perform as required.

When the pulley has a force applied to it, the ball will prevent the pulley from moving with respect to its vertical position on the door. The cord may freely move about the pulley when force is applied to it. The cord attached to the first anchor is placed through the pulley, which redirects its direction. Other devices which can redirect force may be employed. For instance a generally circular disk with a groove radially oriented about the circumference could be adapted to retain the cord and permit sliding movement of the cord thereon.

The cord is then affixed to a second anchor. This second anchor in turn is affixed to a webbing which is designed to encircle the feet. When the webbing is placed about the feet, and the headpiece is on the patient, the patient merely needs to move there feet forward to produce traction on the neck. It is has also been considered that the cord may be lengthened and a loop tied at the distal end. This would replace the second anchor and the webbing designed to encircle the feet.

The anchors, cord and webbing may all be made from any of a host of materials and this application is not intended to be limiting in the choice of materials. As before, any material with suitable material properties may be employed. In this case, the anchor must support certain forces, the webbing must be flexible and able to be affixed by sewing (or an another mechanical fastening arrangement), and the cord must have tensile properties so that it does not break or stretch too far.

The entire apparatus is designed to be placed in a bag which may be easily opened and closed for easy storage, retrieval and setup.

DETAILED DESCRIPTION OF THE FIGURES

Figure 1:
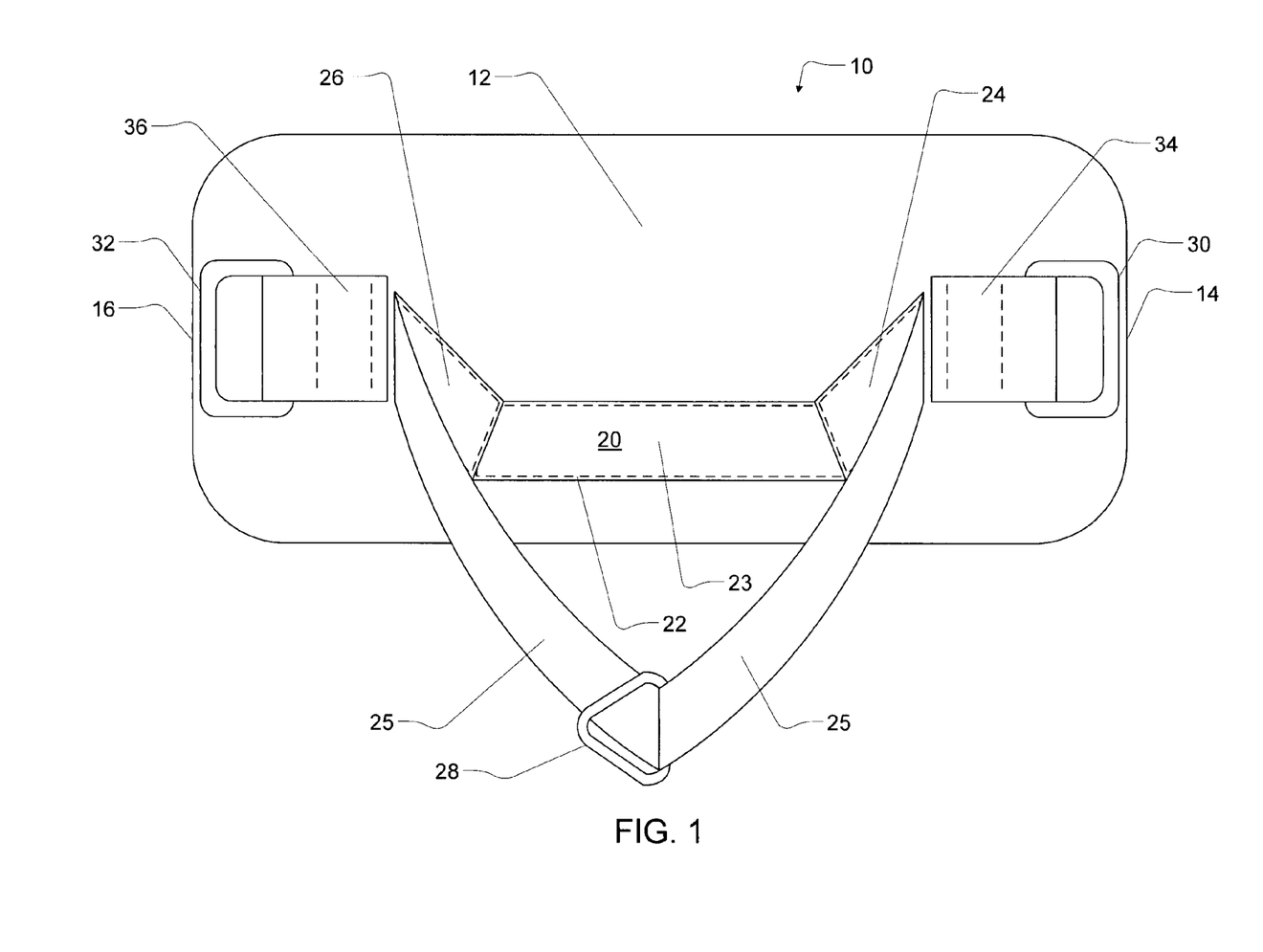
FIG. 1 is a view of the rear element back side of the headpiece.

FIG. 1 is a view of the rear element back side 12 of the headpiece 10. The back side 12 of the rear element 10 includes a right side 14 and a left side 16. A nylon webbing 20 is stitched 22 to the rear element back side 12. The nylon webbing 20 has a right wing 24 and a left wing 26. Both the right wing 24 and the left wing 26 are angularly offset generally as shown by the intermediate or central portion 23. The webbing 20 is no longer attached directly to the rear element back side 12 after the terminus of the right wing 24 and the left wing 26. It is affixed in a sense as both terminating points of the wing elements affix the remaining webbing in what is essentially a loop 25. The patient's head would be placed through loop 25 and the patient's neck would rest approximately on the nylon webbing 20. Loop 25 is secured about a first anchor 28.

The rear element back side 12 includes a right (first) connection element 30 and a left (second) connection element 32. The right connection element 30 is secured to a the rear element back side 12 by a right portion of webbing 34. The left connection element 32 is secured to the rear element back side 12 by a left portion of webbing 36. The right connection element 30 and the left connection element 32 are designed to receive the forehead strap 50 shown best in FIGS. 3 & 4.

Figure 2:
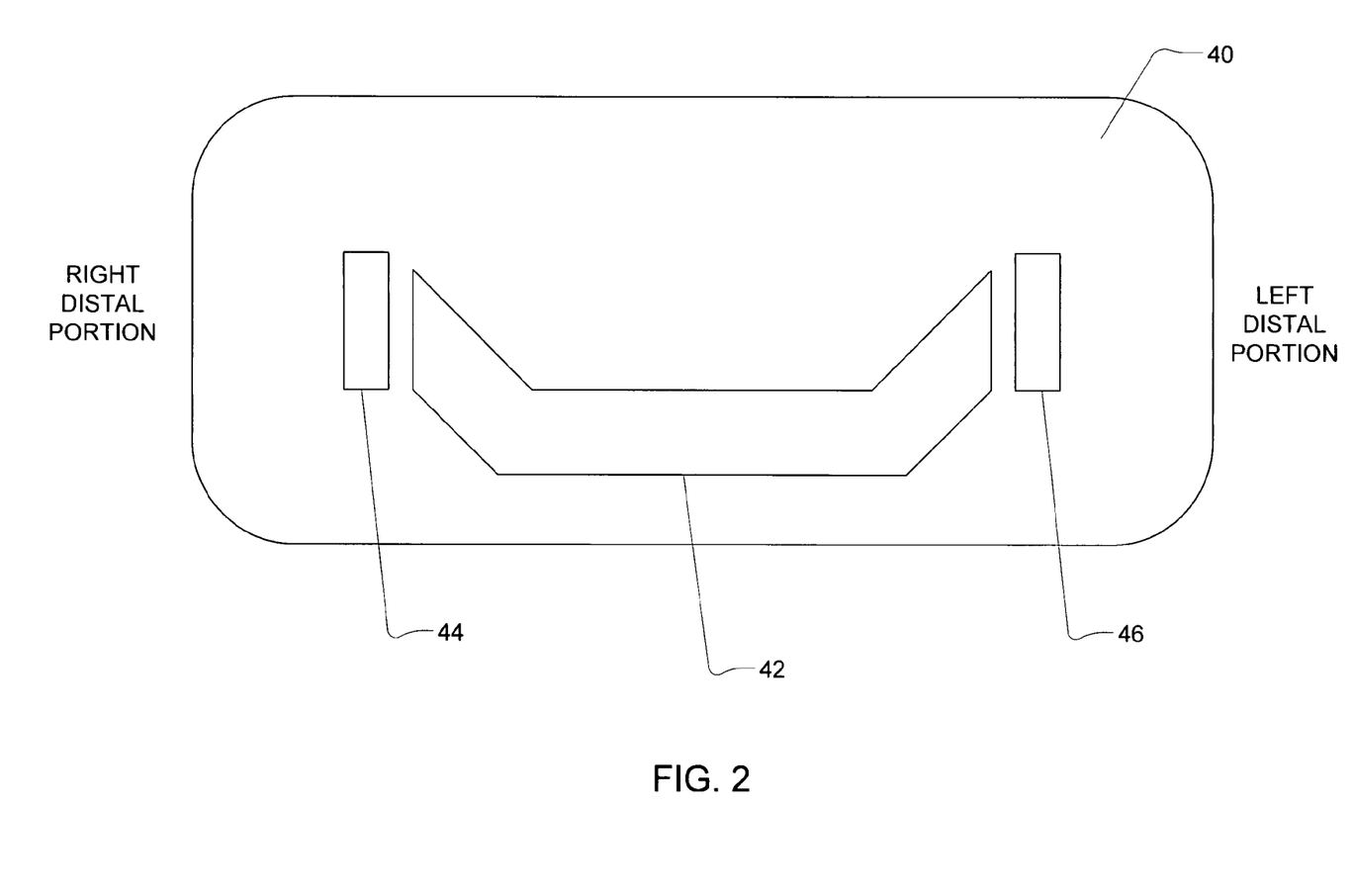
FIG. 2 is a view of the rear element front side of the headpiece.

Referring now specifically to FIG. 2, the rear element front side 40 is shown. Element 42 is the stitching to secure the nylon webbing 20. Element 44 is the stitching to secure the right portion of webbing 34. Element 46 is the stitching to secure the left portion of webbing 36.

Figure 3:
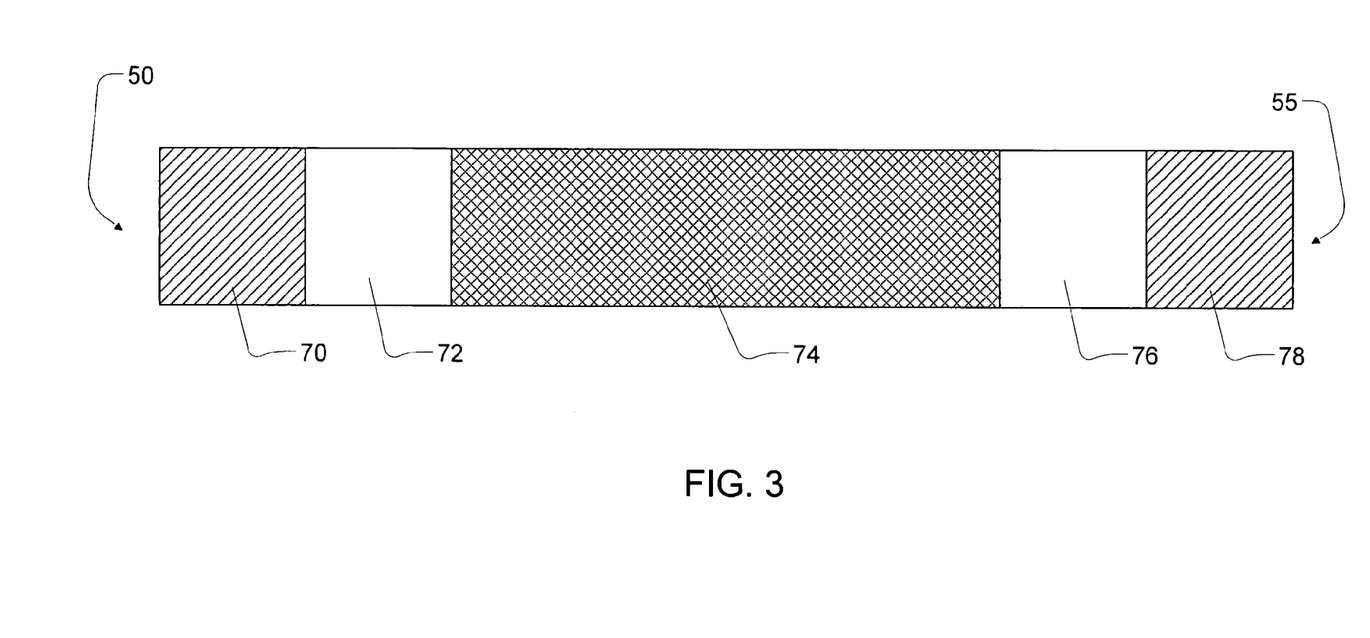
FIG. 3 is a view of the first strap (or forehead strap) second side.
Figure 4:
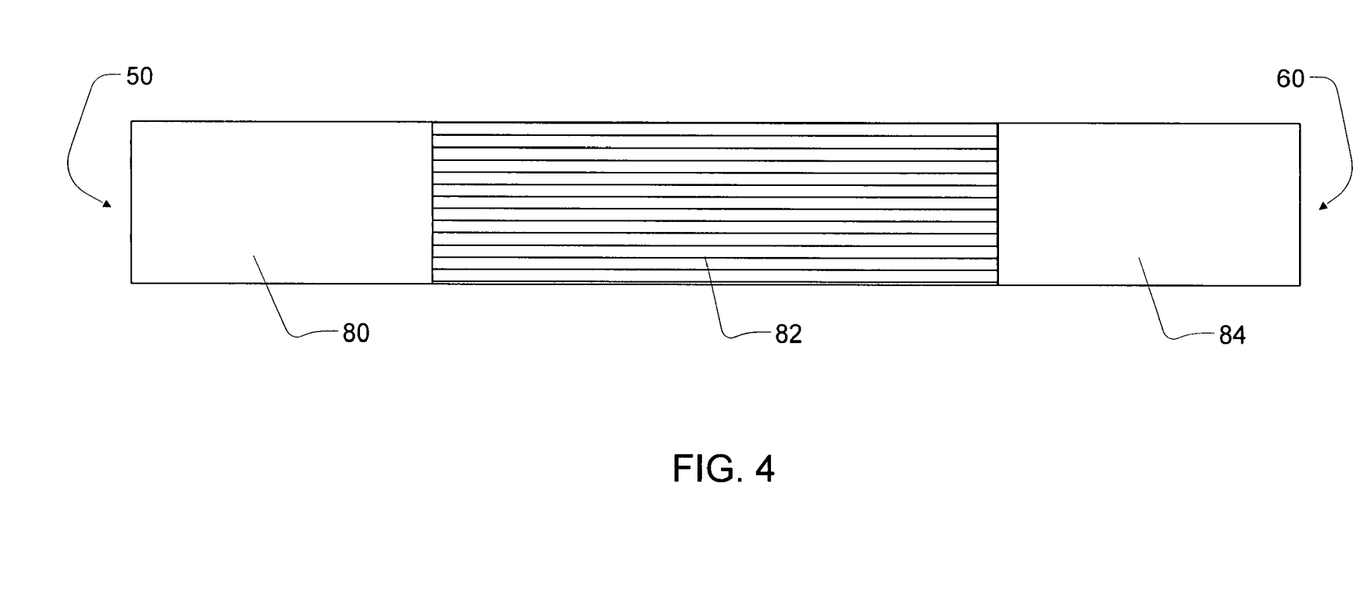
FIG. 4 is a view of the first strap (or forehead strap) first side.

Referring now specifically to FIGS. 3 and 4 the forehead strap 50 is shown. FIG. 3 shows the forehead strap's second side 55 and FIG. 4 shows the forehead strap's first side 60, the first side 60 which will reside against the forehead of the patient.

On FIG. 3, we will examine the structure from left to right. First, along the entire length is a piece of strap. Element 70 is a first hook portion of hook and loop fasteners. Element 72 is a first strap portion. Element 74 is a loop portion of hook and loop fasteners. Element 76 is a second strap portion. Element 78 is a second hook portion.

On FIG. 4 we will once again examine the structure from left to right. Again, the entire length is a piece of strap, this is the same strap discussed in FIG. 4 but is being viewed from the other side. This is the first side 60 which will interface with the forehead of the patient. Starting with element 80, the strap is again shown. Element 82 is padding which is affixed to the strap in order to be comfortable when the strap is tightened about the forehead. Element 84 is the strap again.

Figure 5:
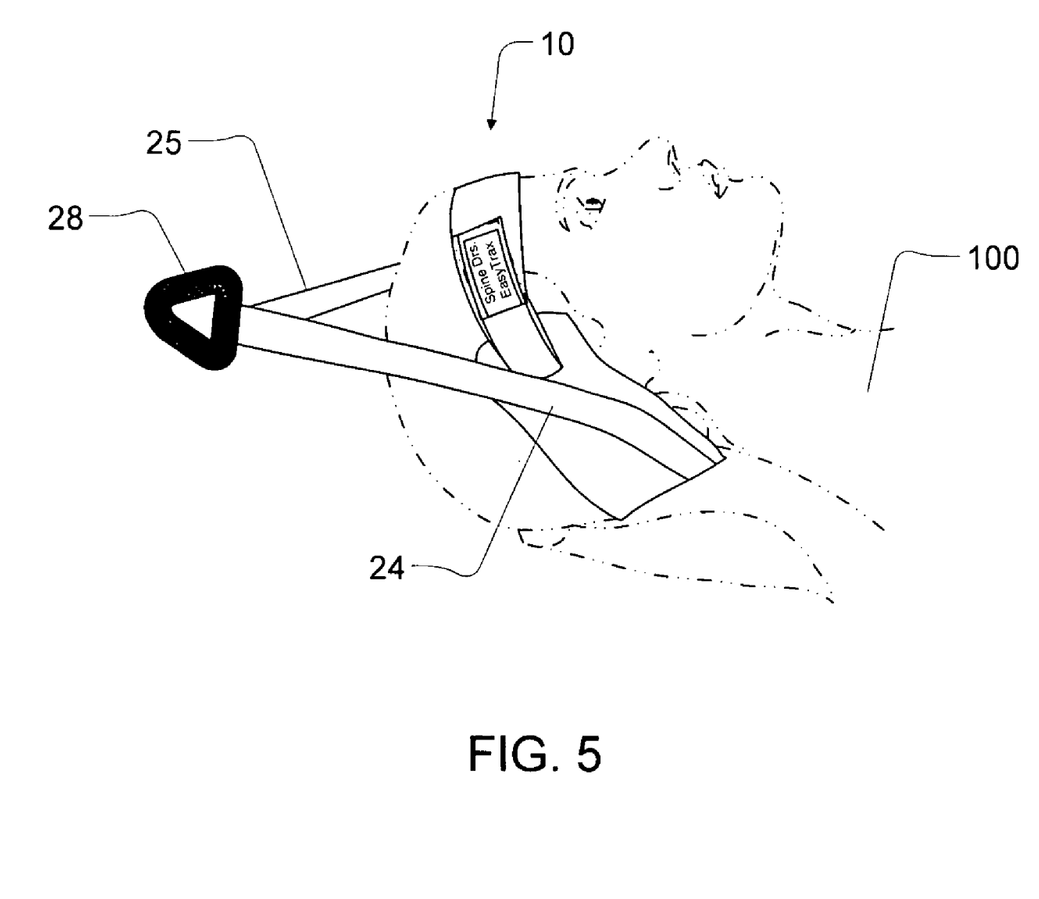
FIG. 5 is a view of the headpiece being applied to the patient's head.

Referring now to FIG. 5, we show the headpiece 10 affixed about the head of a patient 100. The rear element front side 40 is placed about the neck of the patient 100 with the webbing 20 placed at the lowest part of the base of the skull. The forehead strap 50 is then placed on the patient with the padding 82 in direct contact with the forehead.

Right connection element 30 receives element 78 therethrough and the hook fasteners located on element 78 are pulled through and over connection element 30 where they are mated with the loop fasteners on element 74. Left connection element 32 receives element 70 there-through and the hook fasteners located on element 78 are pulled through and over connection element 32 where they are mated with the loop fasteners on element 74.

FIG. 5 shows a portion of the secured webbing 20, the right wing 24 and the loop 25, as well as the first anchor 28.

Figure 6:
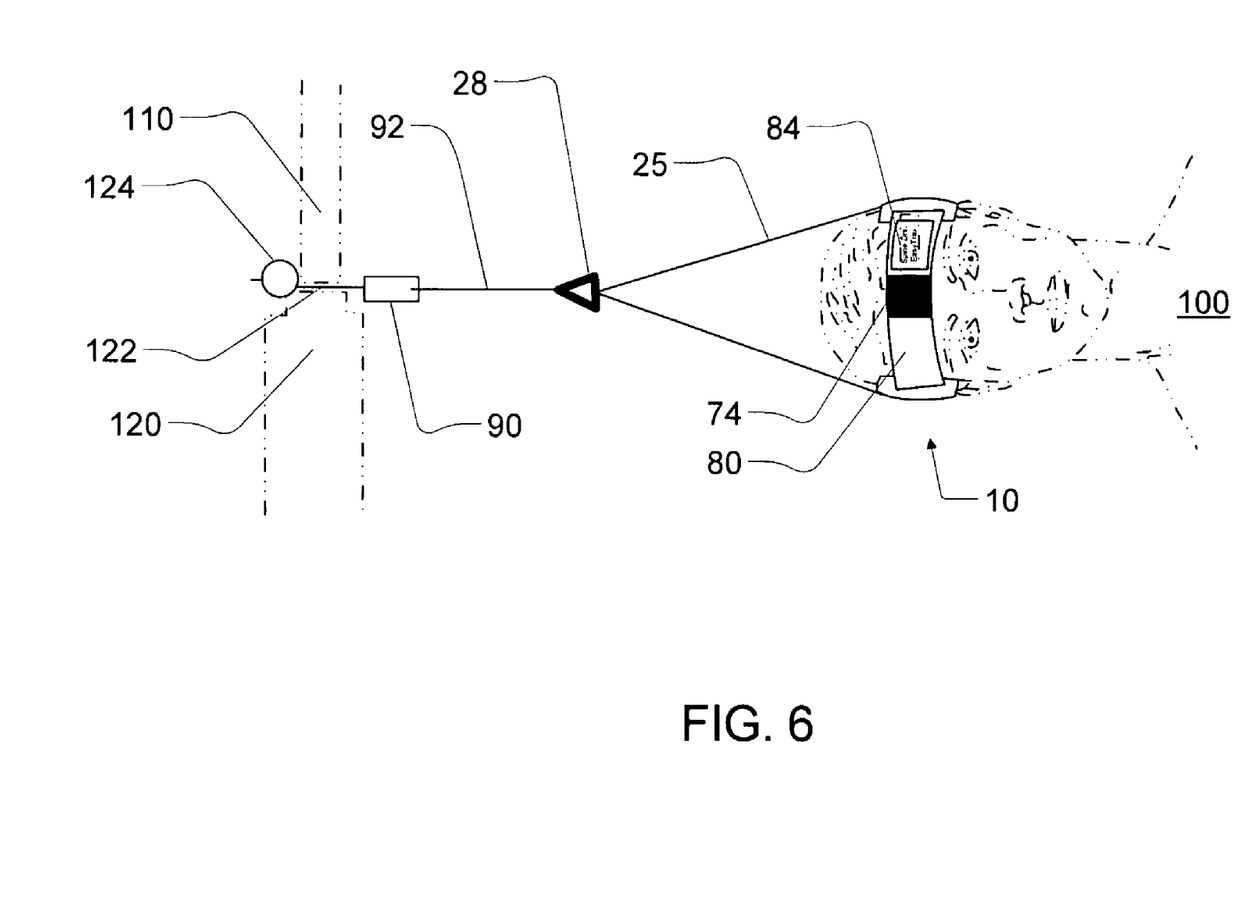
FIG. 6 is a view of the headpiece being attached to the patient's head, further connected by the anchor and cord to the pulley system.

Referring now to FIG. 6, a top view of the headpiece 10 is shown on the patient 100. The forehead strap's first side 60 padding section 82 resides against the patient's forehead. The two end's of the strap are placed through the two connection elements and the hook and loop fasteners are engaged. Since the strap is symmetric, either side may be used and pulled through. In this view, we show the strap 50 with the padding against the forehead, with element 80 being placed through the right connection element 30 and element 84 being placed through the left connection element.

Anchor 28 is affixed to pulley 90 by a cord 92. The pulley 90 in turn is secured intermediate a closed door 110 and a wall 120. The pulley 90 is secured between the door 110 and the wall 120 because it is also affixed to a cord 122 which in turn is affixed to a ball 124. This is shown in more detail in FIG. 7.

Figure 7:
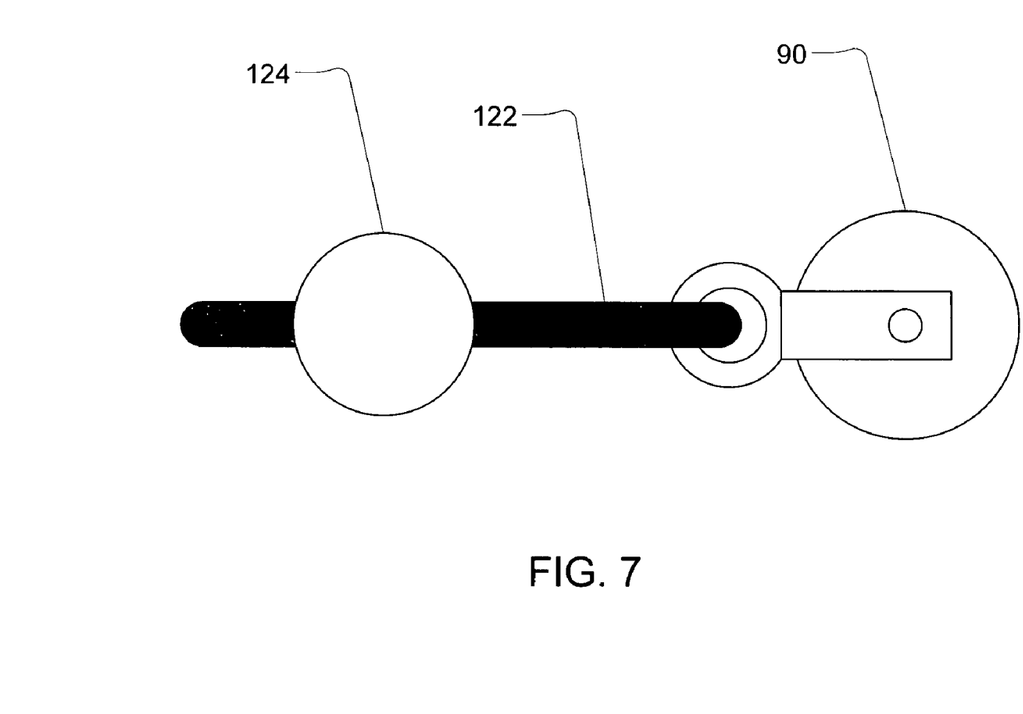
FIG. 7 is a view of the pulley mechanism.

Referring now to FIG. 7, the pulley system is shown. Pulley 90 is affixed by a cord 122 to a ball 124. The cord 122 is placed intermediate a door 110 and a wall 120 and the door 110 is shut, securing the pulley 90 in place. It is to be understood that the cord 122 may be of a different diameter or the same diameter as cord 92. Additionally, cord 122 may be made of the same or a different material than cord 92. Ball 124 may be of any geometric shape that would prevent the cord 122 from being pulled through the shut door 110 and wall 120. Additionally, the pulley system may be placed intermediate other devices which open and close, such as windows, sliding glass doors and the like.

Figure 8:
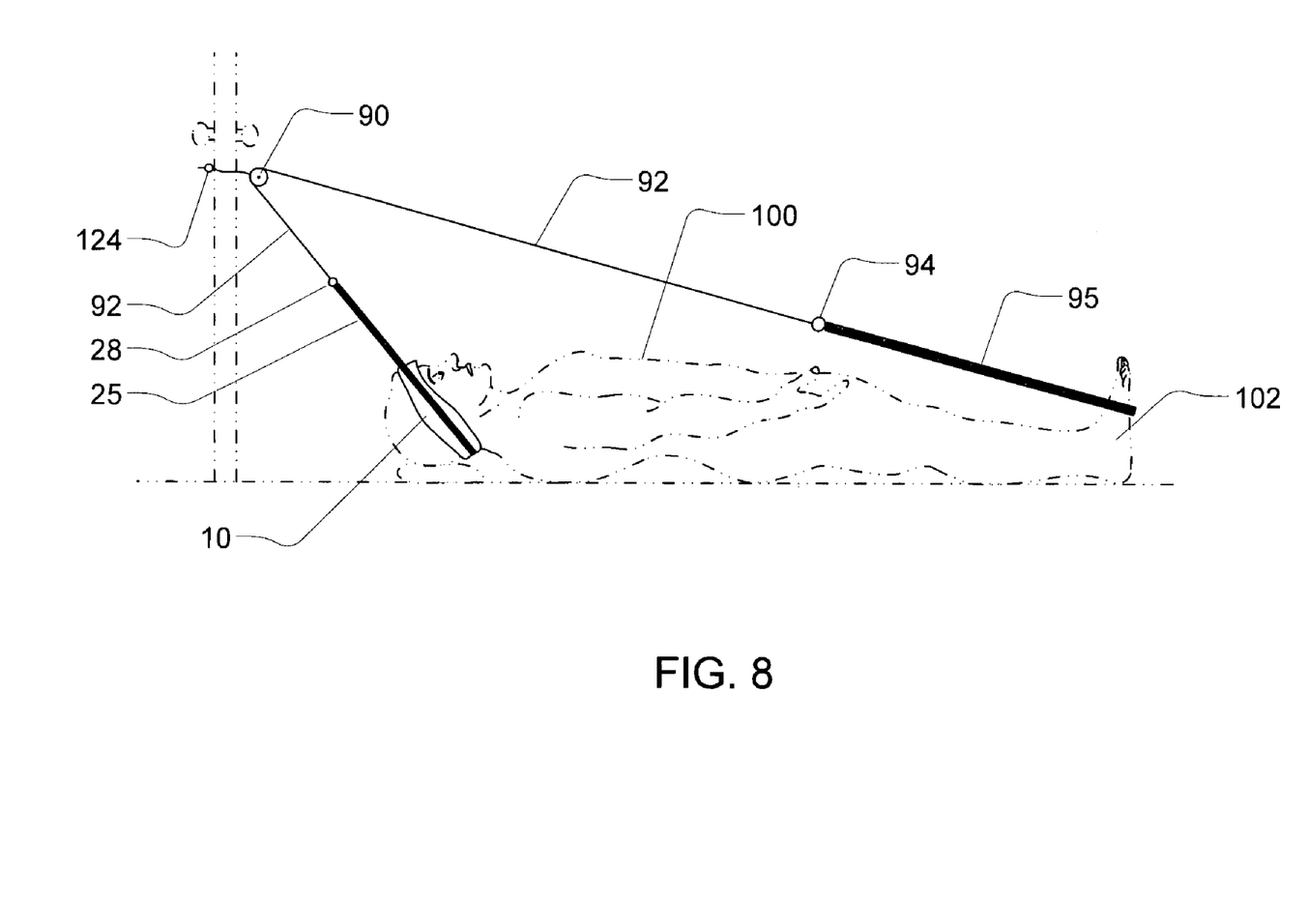
FIG. 8 is a patient employing the self-actuated cervical traction device.

Referring now to FIG. 8, we see the Self-Actuated Cervical Traction Device fully deployed on the patient 100. As seen, the headpiece 10 is placed on the head as previously described. The loop 26 is connected to the first anchor 28, which in turn is affixed to cord 92. Cord 92 passes through the pulley 90 of the pulley system where is passes over the body to a second anchor 94. Second anchor 94 in turn is affixed to a second loop 95. The second loop 95 may also be made from webbing material. The second loop 95 fits about the patient's feet 102. By flexing the legs, the patient may gently place traction on the neck, which would assist in the treatment of a variety of ailments.

One must take care to ensure that the cord 92 is of a proper length for a given patient's physical dimensions. Additionally, one should take care to prevent the opening of the door during therapy.

We claim:

1. A self-actuated cervical traction device for performing traction on a user's neck comprising,
 a headpiece, said headpiece including a first element which is adapted to be placed about the back of the neck of the user,
 said headpiece further including a second element which is adapted to secure said first element on the head of the user,
 said headpiece first element being generally rectangular and having a front side, a back side, a right side and a left side, said headpiece first element right side provided with a first slot and said headpiece first element left side provided with a second slot,
 said headpiece first element back side including a strap affixed thereto, said strap forming a first loop, said headpiece second element being elongated and having a front side, a back side, a right side and a left side, said front side having padding centrally located thereon, said back side including first hook fasteners on a right distal portion, second hook fasteners on a left distal portion, and loop connectors centrally located opposite said padding,
 wherein said headpiece first element is placed about the neck of the user, said headpiece second element is placed on the forehead of the user with the padding lying thereon, said right distal portion is pulled through said first slot and said first hook fasteners are connected to said loop connectors, and further said left distal portion is pulled through said second slot and said second hook fasteners are connected to said loop connectors, thus securing said headpiece to the user,
 said first loop including a first connection anchor,
 said device further provided with a cord, said cord affixed to said first connection anchor,
 a force redirection means, said force redirection means adapted to permit said cord to movably reside thereon,
 a second loop, said second loop including a second connection anchor, said cord further affixed to said second connection anchor, whereby
 said second loop is placed about the user's feet, the user then extends their legs carefully, causing said cord to pull, creating a pull-force, said force redirection means redirecting said pull-force to said first loop by said first anchor, causing said neck to be pulled by said pull-force through said headpiece in a manner replicating traction.

2. A self-actuated cervical traction device for performing traction on a user's neck as claimed in claim 1 wherein said force redirecting device is a pulley.

3. A self-actuated cervical traction device for performing traction on a user's neck as claimed in claim 2 wherein said pulley includes a U-shaped element connected about said pulleys center, said U-shaped element further having a circular element attached thereto said circular element not affecting the rotation of said pulley.

4. A self-actuated cervical traction device for performing traction on a user's neck as claimed in claim 3 whereby said circular element includes a string securely attached thereto said string being further connected to a ball, whereby said string is sized such that when placed in a shut door, said pulley will be secured thereto.

5. A self-actuated cervical traction device for performing traction on a user's neck as claimed in claim 1 wherein said strap is affixed to a portion of said headpiece first element back side.

6. A self-actuated cervical traction device for performing traction on a user's neck as claimed in claim 5 wherein said strap is affixed to said headpiece in such a manner to place said strap proximate the area between the head and the neck.

7. A self-actuated cervical traction device for performing traction on a user's neck as claimed in claim 6 wherein said strap is affixed proximal the lower portion of said headpiece first element said back side.

* * * * *